US005637566A

United States Patent [19]
Walker et al.

[11] Patent Number: 5,637,566
[45] Date of Patent: Jun. 10, 1997

[54] METHOD OF IMPROVING CARCASS QUALITY BY ADMINISTERING GROWTH HORMONE

[75] Inventors: Ian J. Walker, North Balwyn; Roger G. Campbell, Corowa, both of Australia

[73] Assignee: Southern Cross Biotech Pty. Ltd., Dandenong, Australia

[21] Appl. No.: 412,097

[22] Filed: Mar. 28, 1995

Related U.S. Application Data

[63] Continuation of Ser. No. 132,123, Oct. 4, 1993, abandoned, which is a continuation of Ser. No. 963,950, Oct. 19, 1992, abandoned, which is a continuation of Ser. No. 398,070, Aug. 24, 1989, abandoned, which is a continuation-in-part of Ser. No. 309,911, Feb. 10, 1989, abandoned.

[30] Foreign Application Priority Data

| Aug. 24, 1988 | [AU] | Australia | PJ0024 |
| Feb. 8, 1989 | [AU] | Australia | PJ2630 |

[51] Int. Cl.$^6$ .......... A61K 38/00; A61K 38/08; A61K 38/27; C07K 14/00
[52] U.S. Cl. .......... 514/12; 530/324; 530/325; 530/350; 530/399
[58] Field of Search .......... 530/324, 325, 530/350, 399; 514/12, 2

[56] References Cited

U.S. PATENT DOCUMENTS

| 4,670,249 | 6/1987 | Ivy et al. | |
| 4,765,980 | 8/1988 | DePrince et al. | |
| 4,788,144 | 11/1988 | McMullen | |
| 4,792,546 | 12/1988 | Baker | 514/12 |
| 4,857,505 | 8/1989 | Arendt | 514/12 |
| 4,863,736 | 9/1989 | Alain et al. | 424/423 |
| 5,004,728 | 4/1991 | Chalupa et al. | 514/12 |
| 5,015,626 | 5/1991 | Christian et al. | 514/12 |

FOREIGN PATENT DOCUMENTS

| 62522/86 | of 0000 | Australia |
| 529833 | 2/1982 | Australia |
| 0192360 | 8/1986 | European Pat. Off. |
| 01033995 | 8/1986 | European Pat. Off. |
| 0125818 | 4/1987 | European Pat. Off. |
| 0217572 | 4/1987 | European Pat. Off. |
| 0226448 | 6/1987 | European Pat. Off. |
| 0280407 | 8/1988 | European Pat. Off. |
| 0283458 | 9/1988 | European Pat. Off. |
| 2138004 | 10/1984 | United Kingdom |
| WO83/04418 | 12/1983 | WIPO |

OTHER PUBLICATIONS

Bryan et al, "Journal of Animal Science", vol. 76,(5) pp. 1454–1463 (May 1992).
Wettermann et al., *J. Animal Sci.*, 44, 7 (1955).
Ellis, *Endocrinology*, 69, 554 (1961).
Lind et al., *J. Animal Sci.*, 27, 1763 (1968).
Fernandez et al., *FEBS Letters*, 25, 625 (1972).
Scanes, *Monsanto Symposium on Present and Future Trends in Animal Nutrition and Feed Manufacturing Technology*, at p. 35, (1983).
Machlin, *Journal of Animal Science*, 35(4), 794–800 "Effect of Porcine Growth Hormone on Growth and Carcass Composition of the Pig" (1972).
*Chem. Abs.*, 76, Abstract No. 44826x "Endocrine Influences on the Growth and Carcass Quality of Holstein Heifers" (1972).
*Chem. Abs.*, 89, Abstract No. 89: 123558h "Performance, Blood and Carcass Characteristics of Finishing Steers Treated with Trenbolone Acetate and Hexestrol" (1978).
*Chem. Abs.*, 89, Abstract No. 89: 160777z "Relationships of Some Endocrine Measurements of Growth and Carcass Composition of Cattle" (1978).
Wagner et al., *Abstracts of American Society of Animal Science*, Abstract No. 454, 70th ASAS Annual Meeting "Growth Performance, Carcass Deposition and Plasma Hormone Levels in Wether Lambs When treated with Growth Hormone and Thyroprotein" (1979).
Muir et al., *Journal of Animal Science*, 56(6), 1315–1323 "Effects of Exogenous Growth Hormone and Diethylstilbestrol on Growth and Carcass Composition of Growing Lambs" (1983).
Olsen, *Proceedings of the 37th Annual Reciprocal Meat Conference of the American Meat Science Assoc.*, Jun. 17–20, 1984, Lubbock, Texas, 12–18 "Potential for Growth Hormones and Growth Hormone Releasing Factors to Improve Carcass Composition" (1984).
*Chem. Abs.*, 100, Abstract No. 100: 33660b "Performance and Carcass Quality of swine Injected Daily with Bacterially–Synthesized Human Growth Hormone" (1984).
Warwick et al., *Biochem. Soc. Trans.*, 12, 247–248 "Characterization of mRNA sequences encoding Sheep Somatotropin (Growth Hormone) by Cloning a Pituitary Complementary DNA" (1984).
*Chem. Abs.*, 103, Abstract No. 70137u "Potential for Growth Hormones and Growth Hormone Factors to Improve Carcass Composition" (1985).
Wallis et al., *Journal of Endocrinology*, 108, Supplement, Abstract No. 223, "Expression of cDNA for Ovine Growth Hormone in *Echerichia Coli*" (1986).

(List continued on next page.)

*Primary Examiner*—Howard E. Schain
*Assistant Examiner*—P. Lynn Touzeau
*Attorney, Agent, or Firm*—Merchant, Gould, Smith, Edell, Welter & Schmidt

[57] ABSTRACT

The present invention relates to the treatment of an animal to improve carcass quality and/or food conversion efficiency. The invention includes administering to an animal exogenous synthetic growth hormone at a frequency less than daily. The exogenous synthetic growth hormone is not orally administered and is not in a sustained release form. Animals including entire male, female, or castrated male pigs, bovine animals or sheep can be treated in this manner.

11 Claims, No Drawings

OTHER PUBLICATIONS

*Journal of Animal Science*, 66, Suppl. 1, 80th Annual Meeting, Abstract Nos. 151 (Kanis et al.) "Effects of Recombinant Porcine Somatotropin (rPST) on Meat Quality of Pigs"; 152 (Kanis et al.) Effect of Recombinant Porcine Somatotropin (rPST) Treatment on Carcass Characteristics and Organ Weights of Growing Pigs; 153 (Beermann et al.) Comparison of the Effects of Two Recombinant Forms of Porcine Somatotropin (pST) on Pork Composition and Palatability; and 154 (Newcomb et al.) Response to 60 to 100 kg Pigs Treated with Porcine Somatotropin to Different Levels of dietary Crude Protein (1988).

Evock, et al., *Journal of Animal Science*, 66, 1928–1941 "Pituitary Porcine Growth Hormone (pGH) and a Recombinant pGH Analog Stimulate Pig Growth Performance in a Similar Manner" (1986).

*Animal Production*, 46, 487, Abstract No. 15 "Pig Carcass and Pork Sensory Characteristics for Animals given Daily Injections of Natural or Recombinant Porcine Somatotropin from 57 to 103 kg" (1988).

Orian et al., *Nucleic Acids Research*, 16, 9046 (1988).

T. Althen et al., "Metabolic Clearance and Secretion Rates of Porcine Growth Hormone in Genetically Lean and Obese Swine", *Endocrinology*, 99:511 (1976).

J. Arbona et al., "Secretory Patterns and Metabolic Celarance Rate of Porcine Growth Hormone in Swine Selected for Growth", *J. Animal Science*, 66:3086 (1988).

R. Boyd et al., "Titration of the Porcine Growth Hormone Dose Which Maximizes Growth Performance and Lean Deposition in Swine", *J. Anim. Sci.* (Suppl. 1), 63:218 (1986).

R. Boyd et al., "Manipulation of Body Composition", *Diseases of Swine*, Iowa State University Press, Allen Leman et al., editors, Ames, Iowa (1992) at pp. 909–922.

R. Campbell et al., "Interrelationships Between Exogenous Porcine Somatotropin (PST) Administration and Dietary Protein and Energy Intake on Portein Deposition Capacity and Energy Metabolism of Pigs", *J. Anim. Sci.*, 69:1522 (1991).

T. Etherton et al., "Stimulation of Pig Growth Performance by Porcine Growth Hormone: Determination of the Dose–Response Relationship", *J. Anim. Sci.*, 64:433 (1987).

J. McMurty et al., "Serum Growth Hormone (GH) in Barrows Fed Two Levels of Energy and Treated with Porcine GH (pGH) and GH–Releasing Factor (GHRF)", *J. Anim. Sci.*, 65:(Suppl. 1)218 (1988).

METHOD OF IMPROVING CARCASS QUALITY BY ADMINISTERING GROWTH HORMONE

This is a continuation, of application Ser. No. 08/132,123, filed Oct. 4, 1993, now abandoned, which is a continuation of Ser. No. 07/963,950, filed Oct. 19, 1992, now abandoned, which is a continuation of Ser. No. 07/398,070, filed Aug. 24, 1989, now abandoned, which in turn is a continuation-in-part of Ser. No. 07/309,911, filed Feb. 10, 1989, now abandoned.

This invention relates to animal husbandry, and in particular to improving the quality of livestock carcasses.

The quality of meat products is critically related to livestock husbandry and feeding practices, and is an important factor in consumer choice. The desirability to the consumer of a particular type of meat depends upon such parameters as price, tenderness, and appearance.

Nutritional factors, including the perceived "healthiness" of the meat, are an increasingly important influence in this area, and among these a high ratio of lean meat to fat is important.

A high ratio of lean meat to fat is also advantageous in the processing of the meat, since extensive trimming of fat and disposal of fat is avoided.

In addition, a high ratio of lean to fat is advantageous for economy of feed conversion, in that typically greater than four times the feed requirement is necessary to deposit 1 kg of fat compared to that necessary to deposit 1 kg of lean tissue.

In many Countries the nature of the feed raw material and the genotype of the animal result in a relatively inefficient conversion of feed meat, and in an undesirably high proportion of fat both on the surface and within the muscle.

Attempts to improve the ratio of lean to fat have been made using conventional breeding strategies. These have often been expensive, long-term, and not without undesirable side effects, Such as deterioration in meat quality and increase in susceptibility of the target animal to stress.

For example in pig farming, daily administration of growth hormone is known in the prior art to promote increased weight gain and improved carcass quality thereby enhancing the food conversion ratio. Economic projections indicate that by treating pigs with "growth hormone" the quality of meat improves in conjunction with the efficiency and costs of production. Such techniques are illustrated in co-pending Australian patent application no. 62522/86, the entire disclosure which is incorporated herein by reference. Unfortunately, the supply of natural porcine pituitary hormones falls well short of demand and given the limitation imposed by species specificity other natural homologues cannot be used cheaply as substitutes.

It is an object of the present invention to overcome or at least alleviate, one or more of the difficulties related to the prior art.

In a first aspect of the present invention, there is provided a method for the treatment of an animal to improve carcass quality and feed conversion efficiency, which method includes providing
an animal selected from the group consisting of entire male, female and castrated male pigs,
an exogenous synthetic porcine growth hormone, analogues, derivatives, or fragments thereof; and,
administering to the animal at a preselected liveweight and at a preselected constant dose rate depending on the sex of the animal, said exogenous synthetic porcine growth hormone initiated at a liveweight of approximately 35 to 100 kg and when the pig is female or a castrated male, the dose rate is approximately 0.06 to 0.10 mg/kg liveweight/day; and when the pig is an entire male, the dose rate is approximately 0.10 to 0.15 mg/kg liveweight/day.

Preferably the source of synthetic growth hormone is growth hormone in a unit dosage form.

More preferably the preselected generally constant dose rate is from approximately 0.06 to 0.15 mg/kg liveweight/day.

It is to be clearly understood that the use of biological active fragments, analogues, derivatives or metabolites of synthetic porcine growth hormone, and the veterinarily acceptable salts thereof, are within the scope of the invention.

As stated above, the method according to the present invention may be applied to transgenic animals. For such animals, administration of growth hormone may comprise the controlled use of an initiator (promoter, enhancer) fused to the growth hormone gone.

Further, recombinant growth hormone is preferred. A recombinant growth hormone selected from methionyl AA1-190 and AA4-190 has been found to be suitable for most domestic animals including pigs, sheep and cattle.

The preparation of recombinant growth hormone methionyl AA1-190 and AA4-190 is described in Great Britain Patent Application 8701848, the entire disclosure of which is incorporated herein by reference. Methionyl AA1-190 is preferred.

Although the invention is described particularly with reference to pigs, sheep and cattle it will be readily apparent to those skilled in the art that the methods of the invention are applicable to other domestic animals such as buffaloes, horses, goats, deer or rabbits, or to birds such as chickens, ducks, geese and turkeys, and to fish, since all of these respond to growth hormone.

In general, any animal, bird or fish capable of being farmed may be used for the purpose of the invention.

Although it is well known that growth hormone (GH) plays an important part in the control of normal growth, its precise role in the control of growth and of metabolism in domestic animals is not well understood. However, it is known that generally the administration of exogenous GH tends to increase the growth rate in all species studied. The role of GH in domestic animals has been briefly reviewed (C. G. Scanes,: Monasanto Symposium on Present and Future Trends in Animal Nutrition and Feed Manufacturing Technology, Arkansas, 1983).

Pigs currently provide an increasingly important source of meat in a large number of countries. According to usual practice, weaned pigs weighing 25 to 30 kg are transferred to grower shed. Growth rate is relatively constant between 30 and 90 kg, but feed consumption increases significantly. Thus the economy of feed conversion progressively deteriorates as the animals approach the slaughter weight of approximately 90 to 110 kg. During the latter growth phase (60 to 110 kg), the carcass develops its final characteristics, and an increasing proportion of the weight gain is represented by fat. Since the energy requirement for production of fat is approximately 2.4 times greater than that for the production of lean tissue, it is clearly advantageous if a metabolic shift toward production of lean tissue can be achieved.

Several studies have investigated the effect of GH in pigs, with considerable variation in results. Turman and Andrews (J. Animal Sci. (1955) 44 7) injected 45 kg pigs daily with porcine GH, and found that treated pigs showed more efficient feed conversion and had leaner carcasses than controls, however, no increase in total weight gain was observed. Moreover, four out of eleven treated pigs died during the experiment as a result of liver and kidney degeneration. Another study (K. D. Lind, R. D. Howard, D. H. Kropf and B. A. Koch: J. Animal Sci. (1968) 27 1763) showed no effect on 72 kg pigs following treatment with porcine GH.

In a more detailed series of experiments, pigs of initial weight approximately 45 kg were treated daily with a range of GH concentration (L. J. Machlin: J. Animal Sci. (1972) 35 794), until they attained a weight of approximately 95 kg. Daily intramuscular injection of 0.22 or 1.10 mg porcine GH per kg bodyweight resulted in high mortality, with liver and kidney degeneration, gastric haemorrhage, oedema and arthritis. Doses of 0.033, 0.066 or 0.132 mg/kg/day resulted in improved average daily weight gain, efficiency of feed conversion, and lean/fat ratio, although the significance of the differences was variable. FUrthermore, in 95 kg pigs fed a restricted high protein diet, GH treatment at 0.13 mg/kg/day improved the rate of weight gain compared to untreated controls.

More recently, it has been found that daily intramuscular injection for 30 days of 0.022 mg GH/kg liveweight in male pigs initially weighing 32 kg increased the growth rate by about 10%, and improved feed efficiency. There was no difference between treated and control groups with respect to dressing percentage, marbling score, loin eye area, or backfat thickness, while percentage lipid in the longissiums muscle was increased. There were no adverse effects of treatment on the animals.

We have now found that supplementing growth hormone levels in pigs results in improved carcass quality, as assessed by backfat thickness, fat and lean percentage, or loin eye area, optionally together with improved feed conversion efficiency.

No deleterious effect upon the health of the animals was observed, and this was confirmed by pathological examination of all the body tissues of the animals.

In a preferred embodiment the administration of synthetic growth hormone is initiated at a liveweight of approximately 35 to 100 kg, more preferably 50 to 100 kg.

Within the preferred initiation range the improvement in carcass quality is essentially similar to that achieved over the longer period. A greater relative improvement in feed conversion efficiency is noted.

Improvement in carcass quality can be measured as an overall increase in lean tissue content together with an increase in the proportion of lean tissue content may be attributed to an increased overall growth rate, an anabolic effect or a combination thereof.

The increase in the proportion of lean tissue to fat tissue may be attributed both to the anabolic effect and a decrease in fat tissue content.

Specifically, we have surprisingly found that there is a previously unsuspected critical interaction between dose of GH, the time of commencing treatment, the length of treatment, dietary energy supply, and sex of pig. The improved carcass quality in female and castrated male pigs, sheep and cattle was particularly unexpected, since normally they lay down fat more readily than entire males and produce an inferior carcass.

Our studies have shown that treatment according to the present invention enhances the growth rate in treated animals relative to controls. Moreover, the carcass quality is greatly improved and the feed consumption of the animals is lower, as a result of the more efficient utilisation of feed by animals treated with GH. At supra-optimal doses of growth rate is not further enhanced, as apparently an appetite-suppressing effect can become limiting.

Results are essentially similar in terms of carcass quality if GH is given when the pigs initially weigh 50 to 60 kg to those found when treatment is given over a longer period, for example from 35 kg. Surprisingly, it is not necessary to increase the dose rate of GH in order to attain the same improvement in carcass quality over the shorter period. However, an improvement in feed efficiency is more apparent in treated animals over the 35 to 60 kg range.

We have found a striking increase in the proportion of lean meat in treated pigs. In a carcass of 60 to 65 kg dressed weight, for example, this represents an increase of 5 to 6 kg in the amount of meat, especially in the commercially valuable parts of the carcass. The economic desirability of such an improvement is clear.

As discussed above, it has surprisingly been found that within specified parameter ranges for particular animals an increase in lean tissue content together with an increase in the proportion of lean tissue to fat tissue may be achieved.

Preferably where the animal is female or castrated male pig, the dose rate is approximately 0.06 to 0.10 mg/kg liveweight/day.

In an alternative aspect of the present invention, there is provided a method of decreasing fat content of an animal carcass, which method includes:
  providing
    an animal selected from the group consisting of entire male, female and castrated male pigs,
    an exogenous synthetic porcine growth hormone, analogues, derivatives or fragments thereof;
  administering to the animal said exogenous synthetic porcine growth hormone at a generally constant dose rate; wherein when the animal is a female pig, the dose rate is approximately 0.06 to 0.1 mg/kg liveweight/day and the treatment continues for approximately 20 days prior to slaughter; when the animal is an entire male pig, the dose rate is approximately 0.1 to 0.15 mg/kg liveweight/day and the treatment continues for approximately 20 days prior to slaughter; and when the animal is a castrated male pig, the dose rate is approximately 0.06 to 0.1 mg/kg liveweight/day and the treatment continues for approximately 10 days prior to slaughter.

In a particularly preferred embodiment, the treatment is administered in a slow release form, for example in the form of implantable pellets or injectable pellets or injectable emulsion.

In a preferred aspect of the present invention, when the animal is a castrated male pig, the treatment is continued for at least about 20 days prior to slaughter.

Whilst the methods described above may improve the carcass quality characteristics greatly, the utilisation of synthetic porcine growth hormones is extremely expensive and time consuming since it normally requires daily administration of unit dosage amounts of synthetic porcine growth hormone for a period of approximately 30 days or more.

Accordingly, in a further aspect of the present invention, there is provided a method for the treatment of an animal to improve carcass quality and/or food conversion efficiency, which method includes
  providing
    an animal selected from the group consisting of entire male, female and castrated male pigs, entire male, female and castrated male sheep, and entire male, female and castrated male bovine animals;

an exogenous synthetic porcine growth hormone, analogues, derivatives, or fragments thereof; and administering to the animal at a preselected liveweight and at a preselected generally constant dose, depending on the sex of the animal, said exogenous synthetic growth hormone, at intervals of at least one day.

It has been surprisingly found that altering the periodicity of dosing provides a significant improvement in growth performance compared to controls. Whilst we do not wish to be restricted by theory, it is postulated that the modification of periodicity of dosing leads to alteration of the relative, anti-lipogenic and protein stimulatory effects of synthetic growth hormone on adipose and muscle tissue respectively. It is further postulated that high doses of synthetic growth hormone given daily depress lipogenesis and feed intake to such an extent that the associated improvement in growth rate is generally only small and often undetectable.

By altering periodicity to every second, third or fourth day administration that is at intervals of 1, 2 or 3 days, it is postulated that the protein stimulatory effect, which is mediated via another hormone (insulin-like growth factor 1), is maintained but the antilipogenic effect which is direct is reduced.

In a preferred embodiment the administration is initiated at a lower weight of approximately 35 to 100 kg, more preferably 60 to 100 kg. Initiation of administration at a liveweight of of approximately 60 kg is most preferred.

More preferably, the dose is approximately 10 mg of exogenous synthetic porcine growth hormone administered on every second, third or fourth day for a period of approximately 10 to 30 days, more preferably to 30 days.

The exogenous synthetic growth hormone may be an exogenous synthetic porcine, ovine or bovine growth hormone depending on the species of animal to be treated.

Administration of a dose of approximately 10 mg every second day is particularly preferred to maximize growth rate. Administration every fourth day provides a significant improvement in growth rate compared with controls but not the same magnitude if administered more frequently. However compared with controls food conversion efficiency is also improved by a dosage regimen of every fourth day.

In a further preferred aspect of the present invention the preselected generally constant dose used may be a reduced dose relative to that normally used in the prior art.

For example, where a dose rate of approximately 10 mg per day may be standard throughout the industry, the dose may be reduced to approximately 50% or less of the standard dosage. It has surprisingly been found that such a reduction in dose amount has a similar and even enhanced effect on growth rate compared to controls at the high amounts described above. In addition feed conversion efficiency may be significantly improved.

Accordingly, the combination of alteration of dose and periodicity of dosage may be used to alter the relative effects of synthetic growth hormone on growth rate, feed conversion efficiency and carcass quality (fat levels etc.). Thus it is possible to tailor the treatments to different types (genotype strains and sexes) of animals including pigs, sheep and cattle.

Accordingly, in a further preferred aspect of the present invention there is provided a method of further increasing the growth performance of an animal to be treated which method includes subsequently continuing administering the exogenous synthetic porcine growth hormone at an increased dose daily for a further preselected period.

In a particularly preferred form, the exogenous synthetic porcine growth hormone is administered to the animal initially at a dose of approximately 4 to 8 mg at intervals of 1, 2, or 3 days for a period of approximately 10 to 25 days; and subsequently continuing administration at an increased dose of approximately 6 to 10 mg daily for a further period of approximately 5 to 15 days.

It has surprisingly been found that the dosage regimen described above may lead to a further significant improvement in growth rate and food conversion efficiency over the total growth period whilst the later period of daily administration of synthetic growth hormone also leads to a further significant reduction in fat levels thus providing major improvements in carcass quality prior to slaughter.

Preferably the initial period of treatment may extend for approximately 10 to 25 days, more preferably 15 to 20 days. The later period of full dose administration may extend for a further period of approximately 5 to 15 days, more preferably 10 days.

In a still further aspect of the present invention there is provided an animal carcass or part thereof whenever prepared according to the methods described above.

The methods of treatment described above may be provided utilising a veterinary composition including an aqueous buffer solution of approximately 3.3 to 6.6 mg/ml of a source of synthetic growth hormone, analogues, derivatives of salts thereof.

In a preferred aspect of the present invention, the synthetic growth hormone may be provided in a sustained-release form. Any suitable delivery system may be used which will provide sustained release. Accordingly, the present invention provides a sustained release veterinary article including an at least partially soluble carrier, a plurality of at least partially soluble microcapsules embedded therein, and an effective amount of synthetic growth hormone or an analogue, derivative, fragment or salt thereof, within the microcapsule.

The at least partially soluble carrier of the sustained release veterinary article may be a polymeric article. The polymeric article may take the form of an implant or bolus.

A polymer which will function as an adjuvant for the synthetic growth hormone may be used. A water-soluble polymer may be used. The polymer article may preferably degrade in approximately 8 to 24 hours after entering the body of the animal. A polymer of the polyvinyl pyrrolidone type may be used. A polyvinyl pyrrolidone polymer or copolymer may be used. The polymer should be selected to provide sufficient impact strength to withstand the impact of the selected delivery system. Other standard compounding ingredients may be incorporated into the polymer matrix. such compounding ingredients may include fillers and extenders. The polymer matrix may further include other active ingredients. Antibiotics, dietary supplements, drenches and the like may also be included.

The polymeric article may be formed in any suitable manner. The polymeric article may be formed utilising an injection molding technique.

As stated above, the sustained-release implant according to this aspect of the present invention further includes a plurality of at least partially soluble microcapsules embedded in the carrier.

The plurality of microcapsules may be incorporated into the polymeric article during the polymerization step thereof. Alternatively, the microcapsules may be incorporated at the molding stage. For example the polymeric article may be compressed into a desired shape utilising tableting technology. A tablet press may be used. The microcapsules and polymer may be mixed prior to moulding.

The microcapsules may be formed from any suitable at least partially soluble polymeric material. A polyester polymer may be used. Polymers and copolymers of -hydroxy acids and derivatives thereof are preferred.

In a preferred aspect, the microcapsules may be formed from a first polymer or copolymer of glycolic acid, lactic acid, a derivative thereof or mixtures thereof having a relatively low molecular weight and a second polymer or copolymer of slycolic acid, lactic acid, a derivative thereof, or mixtures thereof having a relatively high molecular weight. More preferably the plurality of biodegradable microcapsules are formed in at least two particle sizes.

In a further preferred aspect, the plurality of biodegradable microcapsules include microcapsules having a relatively short degradation rate, a medium-term degradation rate or a relatively long degradation rate or a mixture thereof. As discussed above, degradation rates, and in turn the rate of release of the physiologically active ingredients incorporated therein, may be modified by utilising differing polymeric compositions and/or by modifying the molecular weight of the polymers used.

The synthetic growth hormone may be a synthetic porcine, ovine or bovine growth hormone as described above.

The synthetic growth hormone may be encapsulated within the microcapsules in any suitable manner. The encapsulation process may include mixing the polyester or copolyester with the synthetic growth hormone in a suitable solvent; and causing the polyester the precipitate.

The present invention will now be more fully described with reference to the accompanying examples. It should be understood however, that the description following is illustrative only and should not be taken in any way as a restriction on the generality of the invention described above.

The invention will be illustrated by reference to the following non-limiting examples.

The abbreviations used herein are defined as follows:

GH Growth hormone

ADG Average daily liveweight gain (gm/day)

FCR Feed conversion ratio (kg feed/kg liveweight gain)

ADFC Average daily feed consumption (kg/day)

P2 Backfat Depth of backfat at the P2 position (mm)

Lean tissue % Percentage of eviscerated carcass with head off remaining after fat and bones have been removed Dressing (%) Ratio of hot carcass weight to final liveweight prior to slaughter.

In each experiment, porcine GH, was dissolved in buffer containing 0.05M $Na_2CO_3$ and 0.05M $NaHCO_3$, pH 10 to 11, and administered by intramuscular injection. Control animals received intramuscular injections of the same buffer containing 1% lactose. Unless otherwise stated, the pigs were fed ad libitum on a standard high energy diet supplying 14.3 MJ/kg. Treatment commenced when the animals were approximately the weight stated in each case, and continued until they attained their slaughter weight. The animals were deprived of food and water for 24 hours before slaughter to enable an empty liveweight to be measured.

EXAMPLE 1

Comparison of effect of treatment with natural and recombinant growth hormone.

Table 1 illustrates that the results achieved with female pigs differ only marginally whether a natural or recombinant porcine growth hormone is used for treatment. Overall weight gain is greater with recombinant pGH than with natural pGH.

TABLE 1

Effect of daily GH treatment on female pigs initially weighing 60 kg. The pigs were fed ad libitum and slaughtered when a weight of 90 kgs was reached.

|  | Control | pGH Natural | Recombinant (AA1-190) |
|---|---|---|---|
| Number | 8 | 8 | 8 |
| Average daily gain ADG (gm) | 863 | 1049 | 1109 |
| Feed conversion effiency FCR | 3.50 | 2.54 | 2.57 |
| P2 backfat (mm) | 18.9 | 15.7 | 17.7 |
| Dissected lean: |  |  |  |
| Weight per side (kg) | 17.8 | 18.1 | 18.8 |
| Lean Tissue % | 55.4 | 58.8 | 58.8 |

EXAMPLE 2

The abbreviations used herein are defined as follows:
pGH porcine growth hormone (synthetic)
g/d gram per day Unless otherwise stated, the pigs were fed ad libitum on a standard high energy diet supplying 14.3 MJ/kg.

TABLE 2

Effects of pGH dose and frequency of administration between 60 and 90 kg on the growth performance and carcass P2 fat thickness of female pigs.

| pGH dose (mg/pig) | Frequency of administration | Growth rate (g/d) | Feed:gain | P2 (mm) |
|---|---|---|---|---|
| 0.0 | Control | 920 | 3.06 | 19.3 |
| 5.0 | Daily | 1080 | 2.41 | 14.6 |
|  | 2nd day | 1040 | 2.54 | 15.7 |
|  | 3rd day | 1025 | 2.66 | 17.3 |
|  | 4th day | 1000 | 2.71 | 17.6 |
| 10.0 | Daily | 940 | 2.34 | 12.4 |
|  | 2nd day | 1102 | 2.27 | 12.9 |
|  | 3rd day | 1007 | 2.54 | 16.2 |
|  | 4th day | 970 | 2.72 | 16.9 |

The experimental results are summarised in Table 2. The experiment involved two porcine Growth Hormone (pGH) doses (5 and 10 mg) administered daily, every second day, every third day or every fourth day to female pigs growing from 60 to 90 kg. Ten control pigs (injected with a buffer solution every second day) and six pigs on each of the dose×administration treatments (2×4 factorial arrangement) were used.

They show that by administering the low dose (5 mg) every second or third day we can achieve the same growth rate improvement over controls as daily administration (current technology for pigs) but reduce the amount of material required by ½ and ⅔ respectively. The 5 mg dose every second day also enables a similar improvement in feed:gain to be achieved as daily administration.

At the higher dose (10 mg) changing administration from daily to every second day actually results in more rapid gain and improvement in daily gain over controls than daily administration and the every second day administration treatments give slightly higher proportional improvements in feed:gain compared to daily administration of either 10 mg or 5 mg porcine growth hormone.

Based on these results the preferred employment of the present invention would be to use 5 mg pGH every second day or alternatively a higher dose every third day to obtain maximum improvement in terms of growth rate of feed:gain and considerably lower cost than presently required with daily administration. On a less restrictive basis the preferred technique would be to alter dose and frequency of dosing to maximise improvements in growth rate, feed:gain and carcass quality with respect to the type of pig involved (would include starting weight, strain, sex and genotype).

Results further show that 10 mg pGH administered every second day results in an improvement in growth rate compared with daily administration due to a smaller antilipogenic effect during the earlier stages of growth, and an improvement in growth performance and surprisingly a better improvement in carcass P2 fat thickness than 5 mg administered daily, and similar P2 fat thickness as 10 mg administered daily. This finding has obvious implications with respect to economy of use of PST and ease of administration (every second rather than daily administration of 5 mg/d equivalent).

The findings also show that the effect less frequent dosing treatments in reducing feed: gain and P2 fat thickness declined relative to daily administration. This was expected due to the fact that the antilipogenic effects of the less frequent dosing treatments would be expected to decline in the later stages of growth because the dosage per unit body weight is continually declining at a time when fat deposition is becoming an increasingly greater proportion of total growth resulting in an increased fat: protein ratio and as such less efficient growth (higher feed:gain) and fatter carcasses.

Nevertheless, this did not occur with the 10 mg dose administered every second day probably because at this dose fat deposition was adequately depressed or alternatively protein deposition enhanced to such an extent that the fat:protein ratio was similar throughout the whole growth period (but probably different during earlier and later growth, prior to and subsequent to 14 days) as that of pigs administered 10 mg pGH daily.

The results also show that although the second, third and fourth day treatments at 5 mg/pig and third, and fourth day treatments at 10 mg/pig resulted in proportionately smaller improvements in feed:gain and carcass fatness they were all significantly better than the controls in both respects.

It is here that the findings have other implications because under certain circumstances it may be more economical to use less pGH and not necessarily achieve maximum improvements in growth and carcass quality. For example if you were to treat very lean genotypes or alternatively boars with pGH you may not wish to reduce carcass P2 by 30–40% to achieve a target fat level which may only require a 20% reduction in these leaner animals compared with fatter genotypes and female pigs. For instance, administering 10 mg of pGH/pig every third day for 30 days would, on the basis of these results, improve growth rate 11.4% and reduce feed:gain (feed usage) and carcass P2 fat thickness 13.1 and 10.4% respectively and require a total of only 50 mg of pGH. The data show therefore that dose and dose frequency can be used as tools to tailor pGH technology for different breeds, genotypes and different economical circumstances (depending on price of pGH and relative returns for improvements in growth rate, feed:gain and carcass fatness).

EXAMPLE 3

Because the effects of pGH administration on growth Performance and carcass fat thickness declined as did frequency of dosing, the second experiment was conducted to investigate an alternative dosing strategy involving three doses (4, 6 and 8 mg/pig) and various dosing frequencies for a 30 day period commencing at 60 kg. The basic plan was to investigate if the partial loss of the antilipogenic effect during the later stages of growth with the less frequent dosing practices could be combated by imposing a daily administration treatment during the last 10 days of the 30 day period when fat deposition would normally be increasing in untreated pigs. The various treatments imposed to test this possibility are set out below:

Treatments:

(1) Control—Daily buffer injection for 30 days (2) 4.0 mg pGH/pig—Daily for 30 days (3) 4.0 mg pGH/pig—second day for 30 days (4) 4.0 mg pGH/pig—second day for 20 days and 6 mg daily for 10 days (5) 6.0 mg pGH/pig—Daily for 30 days (6) 6.0 mg pGH/pig—second day for 30 days (7) 6.0 mg pGH/pig—third day for 30 days (8) 6.0 mg pGH/pig—third day for 20 days and 6 mg daily for 10 days (9) 8.0 mg pGH/pig—Daily for 30 days

(10) 8.0 mg pGH/pig—third day for 20 days

(11) 8.0 mg pGH/pig—third day for 20 days and 6 mg daily for 10 days

The total amount of pGH used per pig for the 30 day period was:

| Treatment | pGH (mg/pig) |
|---|---|
| 1 | 0.0 |
| 2 | 120 |
| 3 | 60 |
| 4 | 80 |
| 5 | 180 |
| 6 | 90 |
| 7 | 60 |
| 8 | 102 |
| 9 | 140 |
| 10 | 80 |
| 11 | 116 |

Seven female pigs were allocated to each treatment at 60 kg liveweight. They were offered a single diet ad libitum and liveweight gain and feed intake was recorded weekly. Each pig was killed after 30 days treatment and carcass fat thickness measured at the P2 position (6.5 cm from the mid-line at the level of the last rib).

The results for growth performance and carcass P2 fat thickness are presented in Table 3.

Because of an outbreak of comphlobacter during the experiment a number of pigs exhibited severe diarrhoea and had to be withdrawn from the experiment and treated with antibiotics. The performance of these animals was not included in the results. The number of animals completing the experiment is shown in brackets in Table 3.

TABLE 3

Effect of pGH dose and dosing frequency for 30 days on the growth performance and carcass P2 fat thickness of female pigs commencing at 60 kg liveweight.

| pGH dose (mg/pig) | Dosing 0–20 d | Frequency 20–30 d | | Growth rate (g/d) | Feed:gain | P2 (mm) |
|---|---|---|---|---|---|---|
| 0.0 | Control | | (7) | 944 | 2.91 | 21.5 |
| 4.0 | daily | daily | (6) | 966 | 2.42 | 15.5 |
|  | 2nd d | 2nd d | (5) | 986 | 2.61 | 16.9 |
|  | 2nd d | 6 mg/d | (6) | 998 | 2.32 | 13.9 |
| 6.0 | daily | daily | (6) | 990 | 2.30 | 14.4 |
|  | 2nd d | 2nd d | (6) | 1123 | 2.36 | 16.0 |
|  | 3rd d | 3rd d | (5) | 1050 | 2.52 | 16.8 |
|  | 3rd d | 6 mg/d | (6) | 1050 | 2.27 | 15.0 |
| 8.0 | daily | daily | (5) | 990 | 2.30 | 13.7 |
|  | 3rd d | 3rd d | (5) | 1001 | 2.60 | 17.4 |
|  | 3rd d | 6 mg/d | (6) | 1045 | 2.24 | 14.5 |

The overall findings from the study outlined in Example 3 are:

(i) That regardless of dose or dosing frequency, pGH administration improved growth performance and reduced P2 carcass fatness compared to controls.

(ii) Confirmation of previous claim that at higher doses pGH administration every second day improves growth rate proportionately more than daily administration but gives similar improvement in feed:gain. This is evident from the 6 mg pGH treatments although there was some loss of the antilipogenic effect comparing the P2 values for pigs dosed every second day with those dosed daily.

(iii) That at the three doses tested the implementation of less frequent dosing (second or third day) for 20 days followed by daily dosing (6 mg/pig) during the last 10 days of the 30 day period resulted in carcass fat thickness and feed:gain for the whole period returning to the level of pigs administered pGH daily for the 30 day period.

Surprisingly, at the lowest dose tested (4 mg/pig) dosing pigs every second day for 20 days followed by daily dosing with 6 mg/pig for the last 10 days resulted in slight improvements in feed:gain and carcass P2 fat thickness compared with daily administration for the 30 day period.

Overall, results show that a preferred dosage regimen comprising infrequent dosing for 20 days (second or third day) followed by daily dosing for last 10 days enables similar improvements in growth performance and carcass quality (less fat) to be achieved as daily dosing but significantly reduces pGH usage.

Results are presumably achieved because higher and more frequent dosing during later stages of growth enables the marked increase in fat deposition which normally occurs during this period to be depressed resulting in leaner and more efficient growth.

Finally, it is to be understood that various other modifications and/or alterations may be made without departing from the spirit of the present invention as outlined herein.

We claim:

1. A method for the treatment of an animal to improve carcass quality food conversion efficiency; said method comprising:
    (a) providing an animal selected from the group consisting of entire male, female and castrated male pigs;
    (b) providing an exogenous synthetic porcine growth hormone selected from the group consisting of porcine growth hormone, methionyl AA1-190 porcine growth hormone, and AA4-190 porcine growth hormone; and
    (c) administering to the animal at an initial liveweight of approximately 35 to 100 kg a dose of approximately 0.06 to 0.15 mg/kg liveweight, depending on the sex of the animal, of said exogenous synthetic growth hormone, every second, third or fourth day but not daily, wherein the exogenous synthetic growth hormone is not orally administered and is not in a sustained release form.

2. A method according to claim 1, wherein the administration is initiated at a liveweight of approximately 50 to 100 kg.

3. A method according to claim 2, wherein the exogenous synthetic growth hormone is administered for a period of approximately 10 to 30 days.

4. A method according to claim 3, wherein the exogenous synthetic growth hormone is administered by injection.

5. A method for the treatment of an animal to improve carcass quality food conversion efficiency; said method comprising:
    (a) providing an animal selected from the group consisting of entire male, female and castrated male ovine animal;
    (b) providing an exogenous synthetic ovine growth hormone; and
    (c) administering to the animal at an initial liveweight of approximately 35 to 100 kg a dose of approximately 0.06 to 0.15 mg/kg liveweight, depending on the sex of the animal, of said exogenous synthetic growth hormone, every second, third or fourth day, but not daily, wherein the exogenous synthetic growth hormone is not orally administered and is not in a sustained release form.

6. A method according to claim 5, wherein the exogenous synthetic growth hormone is administered for a period of approximately 10 to 30 days.

7. A method according to claim 6, wherein the exogenous synthetic growth hormone is administered by injection.

8. A method for the treatment of an animal to improve carcass quality food conversion efficiency; said method comprising:
    (a) providing an animal selected from the group consisting of entire male, female and castrated male bovine animal;
    (b) providing an exogenous synthetic bovine growth hormone; and
    (c) administering to the animal at an initial liveweight of approximately 35 to 100 kg a dose of approximately 0.06 to 0.15 mg/kg liveweight, depending on the sex of the animal, of said exogenous synthetic growth hormone, every second, third or fourth day, but not daily, wherein the exogenous synthetic growth hormone is not orally administered and is not in a sustained release form.

9. A method according to claim 8, wherein the exogenous synthetic growth hormone is administered for a period of approximately 10 to 30 days.

10. A method according to claim 9, wherein the exogenous growth hormone is administered by injection.

11. A method for the treatment of an animal to improve carcass quality and/or food conversion efficiency; said method comprising:
    (a) providing an animal selected from the group consisting of entire male, female and castrated male pigs;
    (b) providing an exogenous synthetic porcine growth hormone selected from the group consisting of porcine growth hormone, methionyl AA1-190 porcine growth hormone, and AA4-190 porcine growth hormone; and (c) administering to the animal a single dose of approximately 0.06 to 0.15 mg/kg liveweight, depending on the sex of the animal, of said exogenous synthetic growth hormone, every second, third or fourth day, but not a daily dose, with the proviso that said exogenous growth hormone is not administered orally and wherein the animal is at an initial liveweight of approximately 35 to 100 kg.

* * * * *

UNITED STATES PATENT AND TRADEMARK OFFICE
CERTIFICATE OF CORRECTION

PATENT NO. : 5,637,566
DATED : June 10, 1997
INVENTOR(S) : Walker et al.

It is certified that error appears in the above-identified patent and that said Letters Patent is hereby corrected as shown below:

On page 1, in Reference Cited [56], "01033995" should read --0103395--.

On page 2, line 17, "1986" should read --1988--.

In column 1, line 31, "Countries" should read --countries--.

In column 1, line 38, "Such" should read --such--.

In column 3, line 20, "FUrthermore" should read --Furthermore--.

In column 4, line 2, insert --GH,-- after "doses of".

In column 5, line 25, "60" should read --50--.

In column 11, line 62, claim 1, insert --or-- after "quality".

In column 12, line 19, claim 5, insert --or-- after "quality".

UNITED STATES PATENT AND TRADEMARK OFFICE
CERTIFICATE OF CORRECTION

PATENT NO.   : 5,637,566
DATED        : June 10, 1997
INVENTOR(S)  : Walker et al.

It is certified that error appears in the above-identified patent and that said Letters Patent is hereby corrected as shown below:

In column 12, line 41, claim 8, insert --or-- after "quality".

Signed and Sealed this

Seventeenth Day of March, 1998

Attest:

BRUCE LEHMAN

Attesting Officer

Commissioner of Patents and Trademarks